United States Patent [19]  [11] 3,992,385
Bach et al.  [45] Nov. 16, 1976

[54] 2,3-DIHYDROERGOLINES

[75] Inventors: Nicholas J. Bach; Edmund C. Kornfeld, both of Indianapolis, Ind.

[73] Assignee: Eli Lilly and Company, Indianapolis, Ind.

[22] Filed: Jan. 20, 1975

[21] Appl. No.: 542,142

[52] U.S. Cl. ............................. 260/285.5; 424/261
[51] Int. Cl.² .................................... C07D 457/02
[58] Field of Search ................... 260/293.54, 285.5

[56] References Cited
UNITED STATES PATENTS 3,704,233   11/1972   Eich et al. ....................... 260/285.5
3,732,231   5/1973   Semonsky et al. ................ 260/285.5

FOREIGN PATENTS OR APPLICATIONS 226,379   3/1963   Austria ............................ 260/285.5

*Primary Examiner*—Nicholas S. Rizzo
*Assistant Examiner*—Mary C. Vaughn
*Attorney, Agent, or Firm*—Charles W. Ashbrook; Everet F. Smith

[57] ABSTRACT

Reduction of certain ergoline alkaloid derivatives provides 2,3-dihydroergolines, useful as prolactin inhibitors.

3 Claims, No Drawings

2,3-DIHYDROERGOLINES

BACKGROUND OF THE INVENTION

The ergot alkaloids and their derivatives comprise a group of naturally occuring and semi-synthetic compounds which display a wide variety of pharmacological activities. Most of the ergot alkaloid compounds possess the same basic ring system, namely the tetracyclic nitrogen-containing ring system represented by the formula

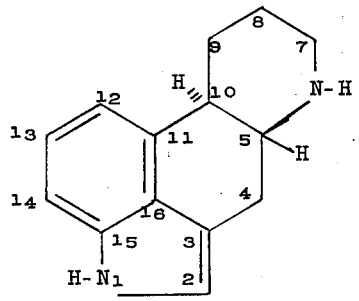

This ring system has been given the trivial name "ergoline," and this name will be used throughout this specification. The term "ergoline" as used herein will include compounds of the above formula having a 9,10-double bond.

Ergot alkaloids and derivatives thereof are often classified into one of two groups; the lysergic acid amides and the clavines. The lysergic acid amides are derivatives of D-6-methyl-8-carboxy-$\Delta^9$-ergoline, a 9-ergolene referred to as lysergic acid, and normally display valuable and unique pharmacologic properties, including in some cases the capacity for inducing abnormal psychic states. Compounds of the clavine class are characterized as being derivatives of D-6-methyl-8-(optionally substituted)methyl-$\Delta^8$ or $\Delta^9$-ergolines, and most of the clavine-related compounds display useful pharmacological properties. For instance, elymoclavine is D-6-methyl-8-hydroxymethyl-8-ergolene, a $\Delta^8$-ergoline, and is useful as an inhibitor of the secretion of the pituitary hormone, prolactin.

Typically, the ergot alkaloids and their derivatives possess a characteristic 2,3-unsaturation, as shown in the above general formula. Only a limited number of 2,3-dihydro-ergot alkaloid derivatives, known as 2,3-dihydroergolines, are known to date. The 2,3-unsaturation of several lysergic acid amides was reduced by Stadler et. al., as described in Helv. Chem. Acta. 47, 756(1964). Similarly, Johnson et al. converted certain amides of lysergic acid to the corresponding 2,3-dihydro, the 9,10-dihydro, and the 2,3,9,10-tetrahydro derivatives. The authors concluded that only 9,10-dihydrolysergamides possessed potent emetic activity; see J. Med. Chem., 16, 532(1973). Kharasch, in U.S. Pat. No. 2,086,559, reported the reduction of ergotocin, a lysergamide derivative, to dihydroergotocin, a useful oxytocic agent. This reduction, however, involved the 9,10-double bond rather than the 2,3-double bond.

Generally, conversion of an ergoline to the corresponding 2,3-dihydro derivative appears to diminish the pharmacological activity of the parent ergoline. It is an object of this invention to provide 2,3-dihydroergolines having equal, if not enhanced, pharmacological properties, as compared with the parent ergoline, especially the ability to inhibit prolactin secretion. The new 2,3-dihydroergolines of this invention also are useful as intermediates leading to other new ergolines.

SUMMARY OF THE INVENTION

This invention is concerned with new compositions of matter. More particularly, this invention provides certain 2,3-dihydroergoline derivatives having the general structural formula

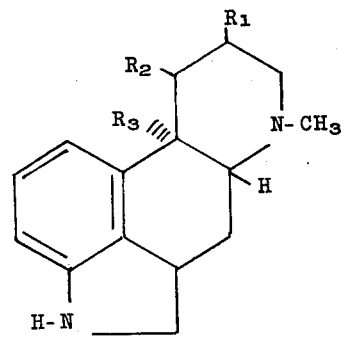

in which $R_1$ is cynanomethyl, hydroxymethyl, $C_1$–$C_4$ alkoxy-carbonyl, or $C_1$–$C_4$ alkanoyloxymethyl; $R_2$ and $R_3$ both are hydrogen, or taken together, form a double bond; except that when $R_1$ is $C_1$–$C_4$ alkoxycarbonyl, $R_2$ and $R_3$ both are hydrogen; and the non-toxic pharmaceutically-acceptable acid addition salts thereof.

DETAILED DESCRIPTION OF THE INVENTION

As used herein, the term "$C_1$–$C_4$ alkoxycarbonyl" encompasses groups having a $C_1$–$C_4$ alkyl group joined to a carbonyl function by an oxygen atom, such as methoxycarbonyl, ethoxycarbonyl, n-propoxycarbonyl, isobutoxycarbonyl, and tert.-butoxycarbonyl. The "$C_1$–$C_4$ alkanoyloxymethyl" group is one in which a hydroxymethyl group is esterified with alkanoic acids having from one to four carbon atoms. Examples of typical "$C_1$–$C_4$ alkanoyloxymethyl" groups include formyloxymethyl, acetoxymethyl, propionoxymethyl, butyroxymethyl, and isobutyroxymethyl.

The 2,3-dihydroergolines provided by the present invention are tetracyclic bases and characteristically exist as white crystalline solids. The new ergoline bases readily form non-toxic pharmaceutically-acceptable acid addition salts by reaction with any of a number of acids which are commonly used in the pharmaceutical art to form non-toxic salts of basic compounds. For example, the compounds of this invention form pharmaceutically-acceptable acid addition salts with inorganic acids such as hydrochloric acid, hydrobromic acid, sulfuric acid, phosphoric acid, nitric acid, sulfamic acid, tetrafluoroboric acid, and related acids. Additionally, salts of the compounds of the above formula readily are formed by reaction of the 2,3-dihydroergoline with any of a number of organic acids, including formic acid, acetic acid, butyric acid, methanesulfonic acid, p-toluenesulfonic acid, maleic acid, succinic acid, tartaric acid, benzoic acid, fumaric acid, glutamic acid, and the like.

The new compounds of this invention are generally prepared by reducing the 2,3-double bond of an appropriately substituted and readily available ergoline to provide the corresponding 2,3-dihydroergoline. Reduction of the 2,3-unsaturated portion of an ergoline refers to the process of adding a hydrogen atom to the 2-carbon atom and to the 3-carbon atom of the ergoline molecule. Such a conversion of an ergoline to the corresponding 2,3-dihydroergoline can be accomplished by any of a number of readily available procedures. Examples of known reduction techniques applicable to an ergoline include catalytic hydrogenation, dissolving metal reduction, metal hydride reduction, and the like.

A typical reduction of an ergoline to provide the corresponding 2,3-dihydroergoline comprises treating the ergoline with a metal such as zinc, in the presence of an acid. The ergoline and the metal can be commingled in about equal weight amounts; however, an excess of metal is customarily employed in the reaction. For example, when zinc metal dust is utilized, it is generally employed in an amount ranging from about 50 to 100 weight excess. The reduction reaction is carried out in acidic media, for example in the presence of a mineral acid such as hydrochloric acid or hydrobromic acid. The amount of acid generally used is a large excess, and often the reaction is carried out simply using the acid as the reaction solvent. Alternatively, the reaction can be conducted in any of a number of solvents, including water, methanol, ethanol, dioxane, dimethyl sulfoxide, and the like. The reduction is best carried out at a temperature below about 100° C., and usually the reaction is complete within about 1 to 12 hours. The product, a 2,3-dihydroergoline, can be isolated either as a free base or as an acid addition salt thereof. To isolate the product, the acidic reaction mixture is filtered to remove unreacted metal, and the filtrate is then made alkaline by the addition of a base such as sodium hydroxide or ammonium hydroxide, thereby converting the 2,3-dihydroergoline salt to the free base form. Typically, the free base so formed is insoluble in the aqueous alkaline solution and separates therefrom. The free base is then extracted into a water-immiscible solvent such as ethyl acetate, diethyl ether, chloroform, or related solvents. Separation of the organic solvent layer followed by evaporation of the solvent then provides the desired 2,3-dihydroergoline as the free base, which is generally a crystalline solid. The free base can alternatively be reacted with an acid, such as maleic or methanesulfonic acid, for instance, thereby providing the 2,3-dihydroergoline as a non-toxic pharmaceutically-acceptable acid addition salt. These salts generally are insoluble in the water-immiscible solvent medium and are readily isolated by filtration. Both the 2,3-dihydroergoline free base and the acid addition salt can be further purified if desired by routine methods, for instance recrystallization from solvents such as methanol, chloroform, hexane, and the like.

As hereinbefore indicated, conversion of an ergoline to the corresponding 2,3-dihydroergoline also can be accomplished by reduction with a metal hydride. An especially convenient and preferred method of reduction of an ergoline is by reaction with sodium borohydride in the presence of an acid. This reduction is a general reaction for indolerelated compounds, and is described in detail by G. W. Gribble in *Abstracts of Paper*, 167th A.C.S. National Meeting, Los Angeles, Mar. 31–Apr. 5, 1974. The reduction reaction is normally carried out by commingling the ergoline and sodium borohydride in an acidic solvent such as trifluoroacetic acid. Typically, the sodium borohydride is employed in an amount ranging from about 50 to 200 molar excess. The reaction is usually conducted at a temperature below about 50° C. and is substantially complete with 1 to 8 hours. The product is customarily isolated by diluting the reaction mixture with water and making the resulting aqueous solution alkaline by adding a base such as potassium hydroxide or ammonium hydroxide. The water-insoluble free base is extracted into an organic solvent such as ethyl acetate or chloroform, and removal of the solvent from the extract provides the desired 2,3-dihydroergoline. If desired, the product can be further purified by recrystallization, chromatography, salt formation, or the like.

The reduction reactions described hereinabove generally provide 2,3-dihydroergolines in which the hydrogen atom at the C-3 position of the ergoline ring system predominantly is in the beta position; however, some of the 2,3-dihydroergoline product often possesses a 3-alpha hydrogen. For example, reduction of D-6-methyl-8-cyanomethylergoline by reaction with sodium borohydride in trifluoroacetic acid provides both the 3-beta hydrogen derivative and the 3-alpha hydrogen derivative. The isomers so formed can be separated, for instance by chromatography or the like, and both compounds display valuable prolactin-inhibiting activity. Broadly speaking, 2,3-dihydroergolines having either a 3-alpha hydrogen or a 3-beta hydrogen atom are encompassed by this invention.

A hereinbefore indicated, the 2,3-dihydroergolines of this invention are useful as intermediates leading to other novel and useful ergoline derivatives. As an example, 2,3-dihydroergolines having the above formula, wherein $R_1$ is a hydroxymethyl group, can be acylated with any of a number of common acylating agents to provide compounds in which $R_1$ is an alkanoyloxymethyl group. More particularly, reaction of a 2,3-dihydro-8-hydroxymethylergoline of the above formula with an acylating agent such as acetic anhydride, or the like, in the presence of a base such as triethylamine or pyridine, provides the corresponding 1-alkanoyl-2,3-dihydro-8-alkanoyloxymethylergoline derivative. These compounds are useful as mild prolactin inhibitors, or they can be converted to the corresponding 1-alkanoyl-2,3-dihydro-8-hydroxymethyl ergoline by basic hydrolysis. For example, reaction of a 1-alkanoyl-2,3-dihydro-8-alkanoyloxymethylergoline with one equivalent of a base such as aqueous sodium or potassium hydroxide effects hydrolysis of the 8-alkanoyloxy group and provides the corresponding 1-alkanoyl-2,3-dihydro-8-hydroxymethyl ergoline prolactin inhibitor. Alternatively, compounds of the above formula in which $R_1$ is hydroxymethyl can be halogenated to provide the corresponding 12,14-dihalo derivative of this invention. More particularly, a 2,3-dihydro-8-hydroxymethylergoline of the above formula can be treated with excess bromine or chlorine in a mutual solvent such as acetic acid, or the like, thereby affording the corresponding 2,3-dihydro-6-methyl8-hydroxymethyl-12,14-dihaloergoline, useful as a prolactin inhibitor.

In a further illustration of their use as intermediates, the diacyl derivatives described hereinbefore can be nitrated to provide novel nitro-ergoline compounds. For example, a 1-alkanoyl-2,3-dihydro-6-methyl-8-alkanoyloxymethylergoline can be converted, by reaction with a nitrating agent, to the corresponding 12-nitro derivative. In particular, 1-acetyl-2,3-dihydro-6-methyl-8-acetoxymethylergoline, for instance, can be treated with an agent such as nitrotetrafluoroborate, in a suitable solvent such as acetonitrile or tetrahydrofuran, thereby providing the corresponding 12-nitro derivative, namely 1-acetyl-2,3-dihydro-6-methyl-8- acetoxymethyl-12-nitroergoline. As before, these nitroergoline derivatives are useful as intermediates, for instance leading to aminoergolines, and as mild pharmaceutical agents, particularly as mild prolactin inhibitors.

The compounds of this invention, in addition to their utility as intermediates, are especially useful as inhibitors of prolactin secretion. Because of their prolactin-inhibiting activity, the new 2,3-dihydroergolines of this invention are useful in the treatment of inappropriate lactation such as undesired postpartum lactation and galactorrhea. The compounds can also be used to treat prolactin-dependent conditions such as mammary adenocarcinomas, prolactin-secreting pituitary tumors, and the like, in which an excess of prolactin is undesirable. Accordingly, the new compounds of this invention can be administered to a subject in order to inhibit prolactin secretion, generally in amounts varying from about 0.01 to about 10 mg. per Kg. of body weight. Doses of the drug will typically be administered at a frequency ranging from 1 to 4 times per day. It will of course be understood that the particular amount of active compound and frequency of administration will be determined in each specific instance, depending on the condition being treated and on its severity. The active ergoline derivative provided by this invention can be administered to a subject by a variety of routes, including both the oral and parenteral routes. The compounds are admixed with routinely used excipients, carriers, and diluents and suitably formulated for convenient oral or parenteral administration. Commonly incorporated excipients, carriers, and diluents include starch, dextrose, sucrose, mannitol, talcum, magnesium stearate, sodium chloride, and others commonly used in pharmacy. For oral administration, the formulated compounds can be pressed into tablets, or encapsulated into empty gelatin capsules, or supplied as a suspension or elixir. The non-toxic pharmaceutically-acceptable salts of the 2,3-dihydroergolines are especially suited for oral administration. Parenteral administration can be effected by formulating the active compound, preferably as a non-toxic pharmaceutically-acceptable acid addition salt, for subcutaneous, intravenous, or intramuscular injection. Generally, the active compound as a salt is admixed with suitable diluents and carriers and dissolved in a solvent such as sterile water or saline for convenient parenteral administration.

In order to more fully demonstrate specific aspects of the invention, the following examples are set forth, presenting detailed experimental results. The examples are not intended to limit the invention in any way to particular aspects set forth therein.

EXAMPLE 1

2,3-Dihydro-6-methyl-8-cyanomethylergoline

A solution of 4.1 g. of 6-methyl-8-cyanomethyl-ergoline in 110 ml. of trifluoroacetic acid was stirred and cooled to 5° C. in a ice-water bath. To the cold solution was added 2.5 g. of sodium borohydride, in 5 equal portions over 1 hour. The reaction mixture was added to 100 g. of ice and the pH of the aqueous reaction mixture was adjusted to 11 by the addition of ammonium hydroxide. The aqueous alkaline reaction mixture was extracted with chloroform. The combined organic extracts were washed with water, dried, and the solvent was evaporated therefrom to provide 2,3-dihydro-6-methyl-8-cyanomethylergoline, M.P. 100°–104° C.

Analysis — Calc. for $C_{17}H_{21}N_3$: Theory: C, 76.37; H, 7.92; N, 15.72. Found: C, 76.14; H, 8.18; N, 15.87.

EXAMPLE 2

2,3-Dihydro-6-methyl-8-methoxycarbonylergoline

A solution of 0.7 g. of 6-methyl-8-carbomethoxyergoline in 50 ml. of trifluoroacetic acid was stirred and cooled to 5° c. in an ice-water bath. To the cold reaction mixture was added 1 g. of sodium borohydride in equal portions over about ½ hour. The reaction mixture was added 50 g. of ice and ammonium hydroxide was added to adjust the pH to 11. The aqueous alkaline reaction mixture was extracted with ethyl acetate, and the combined organic extracts were washed with water, dried, and the solvent was removed therefrom providing 2,3-dihydro-6-methyl-8-carbomethoxy-ergoline as an oil. The oil was added to a column containing 30 g. of florisil, and the column was eluted with chloroform containing 1 percent methanol. Fractions of 50 ml. each were collected, and fractions 25–35 were combined, the solvent was removed therefrom under reduced pressure to afford an oil which was crystallized from diethyl ether and hexane and shown to be 2,3-dihydro-6-methyl-8carbomethoxy-ergoline, M.P. 110°–120° C.

EXAMPLE 3

2,3-Dihydro-6-methyl-8-hydroxymethylergoline

A suspension of 8.13 g. of 6-methyl-8-hydroxymethylergoline and 560 g. of zinc metal dust in 250 ml. of water was cooled to 5° C. in an ice-water bath and stirred. To the cold reaction mixture was added 2500 ml. of concentrated hydrochloric acid dropwise over 6 hours. The acidic aqueous reaction mixture was filtered and the filtrate was made alkaline by the addition of ammonium hydroxide. The aqueous alkaline reaction mixture was extracted with chloroform, and the combined chloroform extracts were washed with water, dried, and the solvent was removed under reduced pressure to afford an oil. The oil was crystallized from methanol, providing 2,3-dihydro-6-methyl-8-hydroxymethylergoline, M.P. 226°–228° C.

Analysis — Calc. for $C_{16}H_{22}N_2O$: Theory: C, 74.38; H, 8.58; N, 10.84. Found: C, 74.48; H, 8.45; N, 10.61.

EXAMPLE 4

1-Acetyl-2,3-dihydro-6-methyl-8-acetoxymethylergoline

A solution 1 g. of 2,3-dihydro-6-methyl-8-hydroxymethylergoline in 50 ml. of pyridine containing 25 ml. of acetic anhydride was stirred at 25° C. for 15 hours. The reaction mixture was added to 100 ml. of water, and the pH of the aqueous layer was adjusted to 10 by the addition of ammonium hydroxide. The aqueous alkaline reaction mixture was extracted with ethyl acetate, and the organic extracts were combined, washed with water, dried, and the solvent was removed therefrom under reduced pressure to provide an oil. The oil was crystallized from methanol, affording 1-acetyl-2,3-dihydro-6-methyl-8-acetoxymethyl-ergoline, M.P. 172°–177° C.

Analysis — Calc. for $C_{20}H_{26}N_2O_3$: Theory: C, 70.14; H, 7.65; N, 8.17. Found: C, 69.97; H, 7.47; N, 7.89.

EXAMPLE 5

2,3-Dihydro-6-methyl-8-hydroxymethyl-12,14-dibromo-ergoline

A solution of 790 mg. of 2,3-dihydro-6-methyl-8-hydroxymethylergoline in 50 ml. of acetic acid was stirred at 25° C. while a solution of 2 g. of liquid bromine in 10 ml. of acetic acid was added dropwise over 15 minutes. The reaction mixture was stirred for ½ hour and then added to 50 ml. of water. The aqueous reaction mixture was made alkaline by the addition of ammonium hydroxide, and the product was extracted from the aqueous alkaline solution into chloroform. The combined organic extracts were washed with water, dried, and the solvent was removed therefrom under reduced pressure to afford 2,3-dihydro-6-methyl-8-hydroxymethyl-12,14-dibromoergoline.

EXAMPLE 6

D-1-acetyl-2,3-dihydro-6-methyl-8-acetoxymethyl-12-nitro-ergoline

A solution of 600 mg. of D-1-acetyl-2,3-dihydro-6-methyl-8-acetoxymethylergoline in 100 ml. of acetonitrile was stirred at 24° C. while 240 mg. of nitrotetrafluoroborate was added in one portion. The reaction mixture was stirred at 24° C. for 1 hour, and then added to 100 ml. of water. The aqueous solution was made alkaline to pH 11 by the addition of ammonium hydroxide, and the aqueous alkaline solution was extracted several times with ethyl acetate. The combined organic extracts were washed with water, dried, and the solvent was evaporated therefrom under reduced pressure, affording a white solid product. The product was recrystallized from methanol to afford D-1-acetyl-2,3-dihydro-6-methyl-8-acetoxymethyl-12-nitro-ergoline. M.P. 174°–176° C.

Analysis — Cal. for $C_{20}H_{25}N_3O_5$ : Theory: C, 62.00; H, 6.50; N, 10.85. Found: C, 61.83; H, 6.26; N, 10.62.

We claim:

1. D-2,3-dihydro-6-methyl-8-hydroxymethyl-12, 14-dibromo-ergoline.
2. D-1-acetyl-2,3-dihydro-6-methyl-8-acetoxymethyl-ergoline.
3. D-1-acetyl-2,3-dihydro-6-methyl-8-acetoxymethyl-12-nitro-ergoline.

\* \* \* \* \*